(12) United States Patent
Koike et al.

(10) Patent No.: US 8,143,359 B2
(45) Date of Patent: Mar. 27, 2012

(54) ORGANIC SILICONE COMPOUND

(75) Inventors: Noriyuki Koike, Takasaki (JP); Takashi Matsuda, Annaka (JP); Hirofumi Kishita, Annaka (JP)

(73) Assignee: Shin-Etsu Chemical Co., Ltd., Tokyo (JP)

(*) Notice: Subject to any disclaimer, the term of this patent is extended or adjusted under 35 U.S.C. 154(b) by 283 days.

(21) Appl. No.: 12/620,782

(22) Filed: Nov. 18, 2009

(65) Prior Publication Data
US 2010/0160588 A1    Jun. 24, 2010

(30) Foreign Application Priority Data

Dec. 18, 2008 (JP) ................... 2008-322434
Jun. 29, 2009 (JP) ................... 2009-154291

(51) Int. Cl.
*C08F 30/08* (2006.01)

(52) U.S. Cl. ........ 526/279; 526/242; 526/247; 526/248; 526/291; 526/292.9; 526/293; 526/294; 526/310; 526/312; 526/332; 526/333; 526/334; 556/413; 556/436; 556/465; 570/123; 570/125; 570/126; 570/127; 570/138; 570/162; 528/10; 528/19; 528/33; 528/36; 528/42; 528/43; 528/367; 528/401; 528/422

(58) Field of Classification Search ............ 526/242, 526/247, 248, 279, 291, 292.9, 293, 294, 526/295, 310, 312, 332, 333, 334; 528/10, 528/19, 33, 36, 42, 43, 367, 401, 422; 556/413; 556/436, 465; 570/123, 125, 126, 127, 138, 570/162

See application file for complete search history.

(56) References Cited

FOREIGN PATENT DOCUMENTS

EP    0 725 113 A1    8/1996
JP    9-20786 A       1/1997

OTHER PUBLICATIONS

Kirpichenko, S. V., Abrosimova, A. T., Albanov, A. I., Voronkov, M. G., "Electrophilic Cyclization of Dimethyl(omega-phenylaminoalkyl)alkenylsilanes". Russian Journal of General Chemistry 2001, 71(12), 1874-1878.*
Search Report mailed Feb. 22, 2010 for European application No. 09177509.8.
Voronkov, M. G. et al: "Aminomercuration-demercuration of dimethyl(chloroalkyl)alkenylsilanes as a route to azasilacycloalkanes", Journal of Organometallic Chemistry, vol. 326, No. 2, 1987, pp. 159-167, XP002568124.

* cited by examiner

*Primary Examiner* — Vasu Jagannathan
*Assistant Examiner* — Richard A Huhn
(74) *Attorney, Agent, or Firm* — Birch, Stewart, Kolasch & Birch, LLP

(57) ABSTRACT

The purpose of the present invention is to provide an organic silicon compound which has a vinyl group more reactive than those of the conventional organic silicon compounds and can be bonded with another compound.

Figure 1:
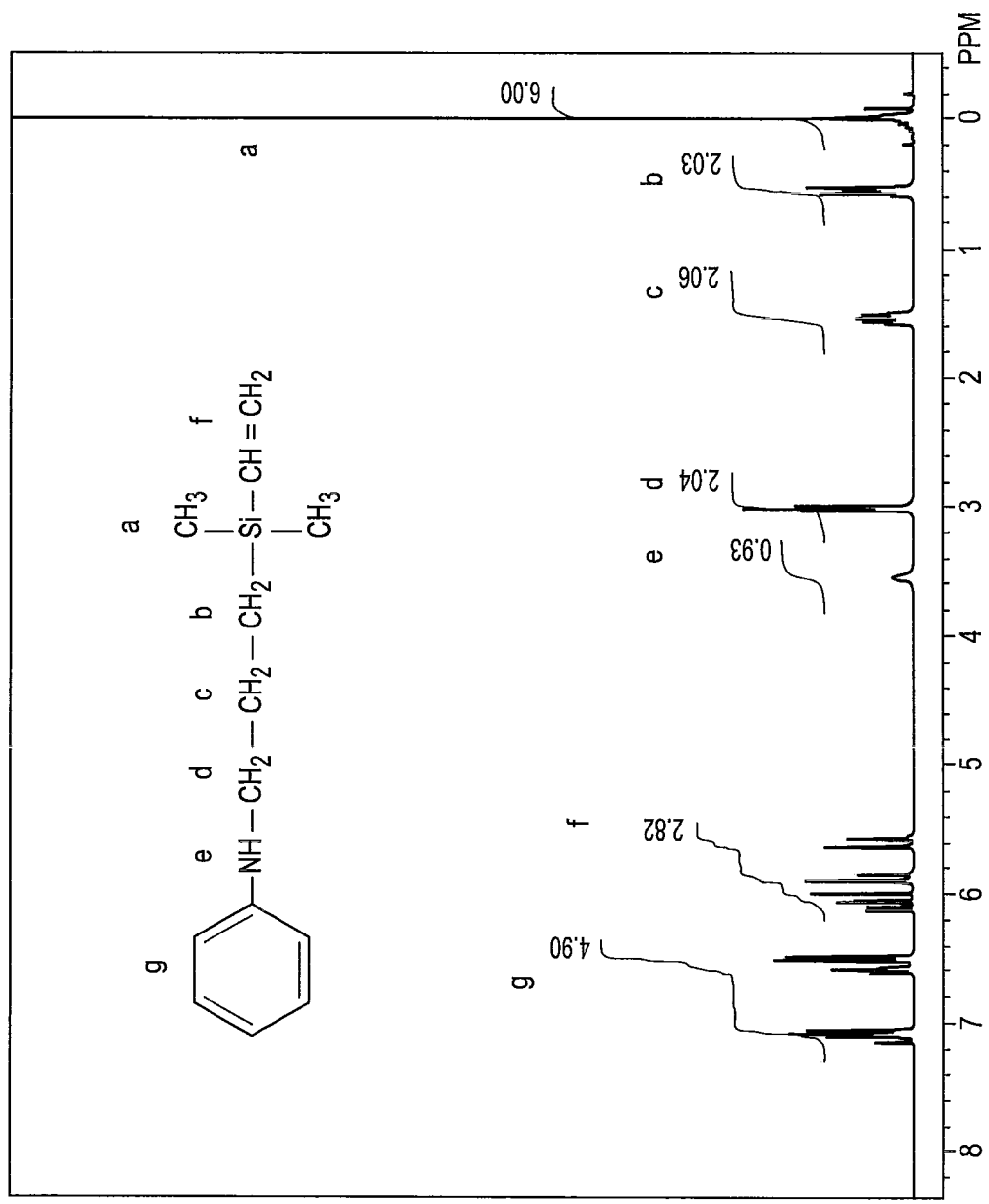

The present organic silicon compound is represented by the following formula (1),

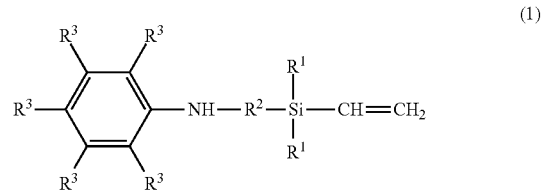

wherein $R^1$ is, independently of each other, a vinyl group or an alkyl group having 1 to 4 carbon atoms, $R^2$ is an alkylene group having 3 to 6 carbon atoms, and $R^3$ is, independently of each other, a hydrogen atom or an alkyl group having 1 to 4 carbon atoms and optionally substituted with one or more fluorine atoms.

3 Claims, 3 Drawing Sheets

ORGANIC SILICONE COMPOUND

CROSS REFERENCES

This application claims the benefits of Japanese Patent Application Nos. 2008-322434 filed on Dec. 18, 2008 and 2009-154291 filed on Jun. 29, 2009, the contents of which are hereby incorporated by reference.

FIELD OF THE INVENTION

The present invention relates to an organic silicon compound having a secondary amino group and a vinyl group bonded to a silicon atom and to an amide derivative thereof. Particularly, the present invention relates to an organic silicon compound wherein a nitrogen atom in the afore-mentioned amino group is linked with the afore-mentioned silicon atom via an alkylene group having a particular number of carbon atoms, whereby the organic silicon compound and the amide derivative thereof do not cause hydrolysis and their vinyl group is more reactive than that of conventional organic silicon compounds.

BACKGROUND OF THE INVENTION

As an organic silicon compound having a secondary amino group and a vinyl group which is bonded to a silicon atom, an aniline derivative having a vinyl group is known from Patent Literature 1. The compound is used for modifying a polymer such as perfluoropolyethers, utilizing the reactivity of the amino group. The modified polymer has a vinyl group and, therefore, can form cross linking by hydrosilylation with a compound which has an Si—H bond. The resulting cross-linked product is used as a rubbery material, paint and a releasing agent (Patent Literature 2).
[Patent Literature 1] Japanese Patent Application Laid-Open No. Hei-9-20786
[Patent Literature 2] EP 0725113 A1

DISCLOSURE OF THE INVENTION

Problems to be Solved by the Invention

Compounds which can be cross-linked by hydrosilylation are cross-linked by heating. A lower heating temperature is preferred for less heat-resistant substrates and for higher productivity. Therefore, the purpose of the present invention is to provide an organic silicon compound which has a vinyl group more reactive than those of the conventional organic silicon compounds and can be bonded with another compound, such as a fluorine-containing polymer. The compound where a vinyl group has been bonded using the afore-mentioned organic silicon compound, for instance, fluorine-containing polymer, can be cross-linked at a lower temperature than the conventional organic silicon compounds because the vinyl group of the present compound is more reactive than that of the conventional ones.

Means to Solve the Problems

The present inventors have synthesized an organic silicon compound having a secondary amino group and a vinyl group bonded to its silicon atom, which vinyl group is more reactive than that of conventional organic silicon compounds. In the present compound, the nitrogen atom in the afore-mentioned amino group is linked with the afore-mentioned silicon atom via an alkylene group having a particular number of carbon atoms, whereby electron density on the vinyl group is increased and, therefore, the reactivity in hydrosilylation is elevated. When this compound is reacted with, for instance, a fluorine-containing polymer, the organic silicon compound having a vinyl group whose reactivity in hydrosilylation is elevated can be bonded with the afore-mentioned polymer to obtain a polymer whose cross-linking can take place at a temperature lower than in a case where conventional organic silicon compounds are used.

Namely, the present invention is an organic silicon compound represented by the following formula (1),

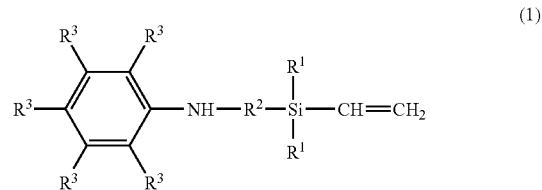

wherein $R^1$ is, independently of each other, a vinyl group or an alkyl group having 1 to 4 carbon atoms, $R^2$ is an alkylene group having 3 to 6 carbon atoms, $R^3$ is, independently of each other, a hydrogen atom or an alkyl group having 1 to 4 atoms and optionally substituted with one or more fluorine atoms.

The present invention also provides an amide derivative of the afore-mentioned organic silicon compound.

Effects of the Invention

The nitrogen atom in the afore-mentioned organic silicon compound is bonded with the silicon atom via an alkylene group having a particular number of carbon atoms and, thereby, the silicon compound does not cause hydrolysis and the vinyl group is highly reactive. Accordingly, a compound having a highly reactive vinyl group can be bonded with another compound, for instance a fluorine-containing polymer, to obtain a compound which can be cross-linked at a temperature lower than in a case where conventional organic silicon compounds are used.

BRIEF DESCRIPTION ON THE DRAWINGS

Figure 2:
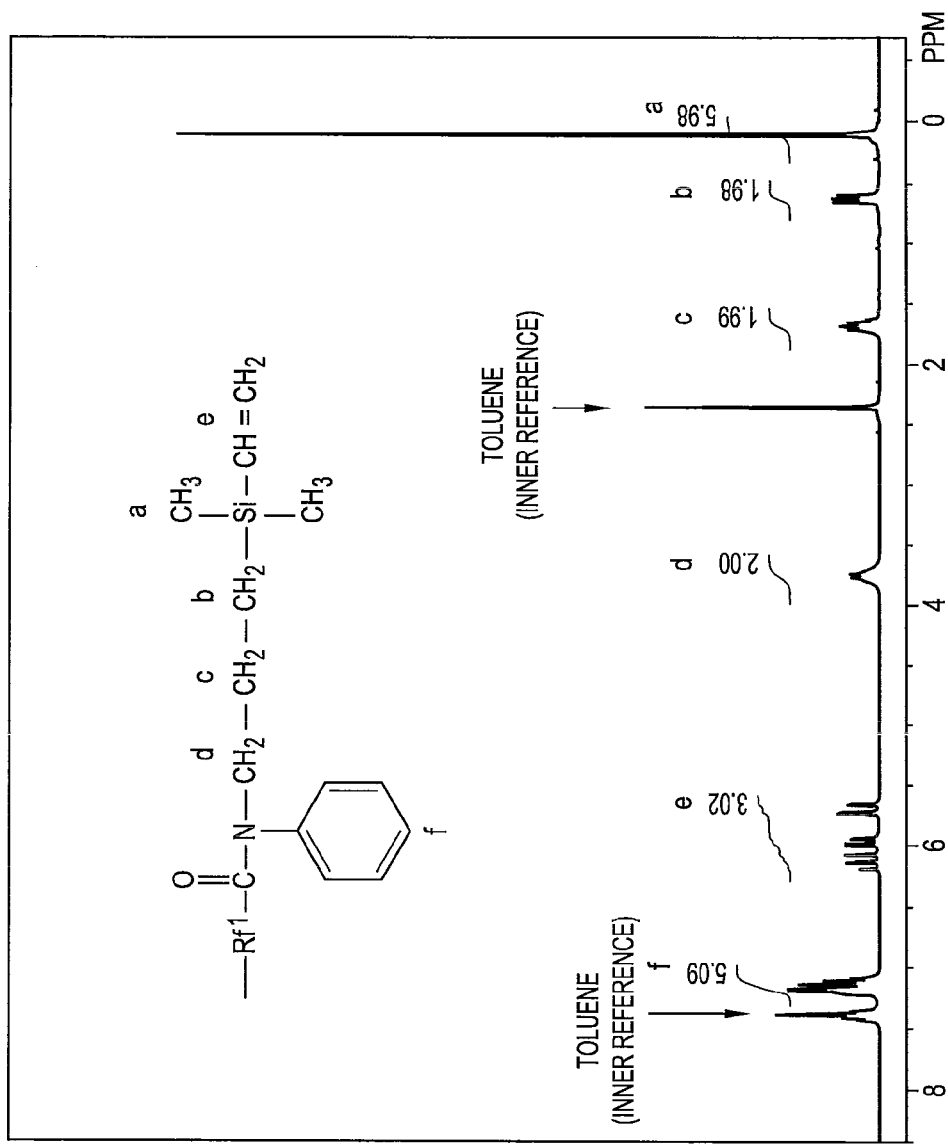
Figure 3:
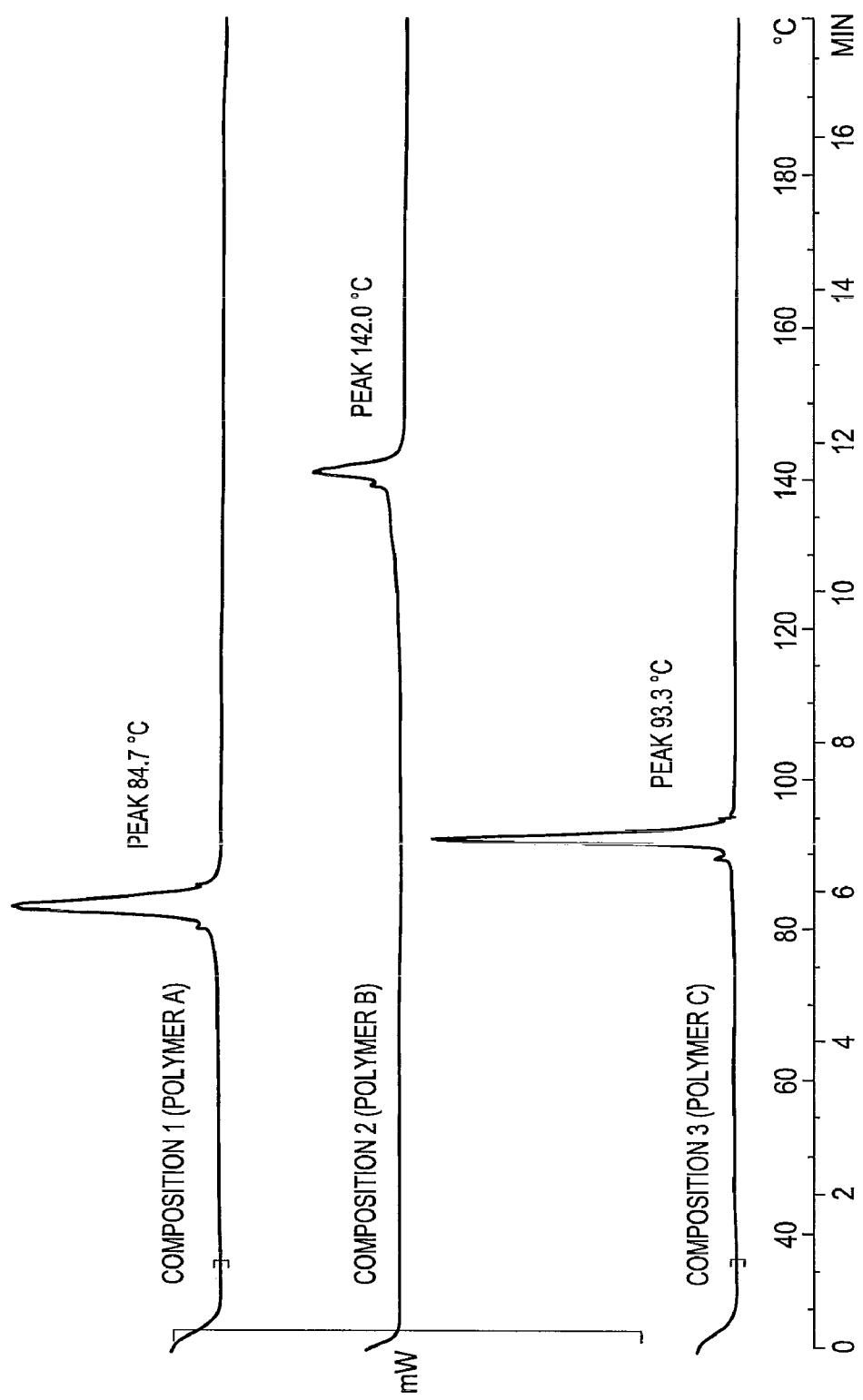

FIG. 1 shows $^1$H-NMR spectra of compound A prepared in Example 1.
FIG. 2 shows $^1$H-NMR spectra of polymer A prepared in Example 2.
FIG. 3 is a DSC chart for compositions 1, 2, and 3, each comprising polymers prepared in Example 2 and Comparative Examples 1 and 2, respectively.

BEST MODES TO WORK THE INVENTION

In the afore-mentioned formula (1), $R^1$ is, independently of each other, a vinyl group or an alkyl group having 1 to 4 carbon atoms, that is, a group selected from the group consisting of a methyl group, an ethyl group, a propyl group and a butyl group. Preferably, $R^1$ is a methyl group. $R^2$ is an alkylene group having 3 to 6 carbon atoms. It is difficult to prepare a silicon compound wherein the number of carbon atoms in $R^2$ is less than the afore-mentioned lower limit and, meanwhile, a silicon compound wherein the number of carbon atoms in $R^2$ exceeds the afore-mentioned upper limit has such a drawback that the silicon compound is easily oxidized and, therefore, its heat resistance is worse. Preferably, $R^2$ is a propylene group.

$R^3$ is, independently of each other, a hydrogen atom or an alkyl group having 1 to 4 carbon atoms and optionally substituted with one or more fluorine atoms, such as a methyl group and trifluoromethyl group. Preferably, $R^3$ is a hydrogen atom or a trifluoromethyl group.

Examples of the compounds represented by formula (1) will be shown below.

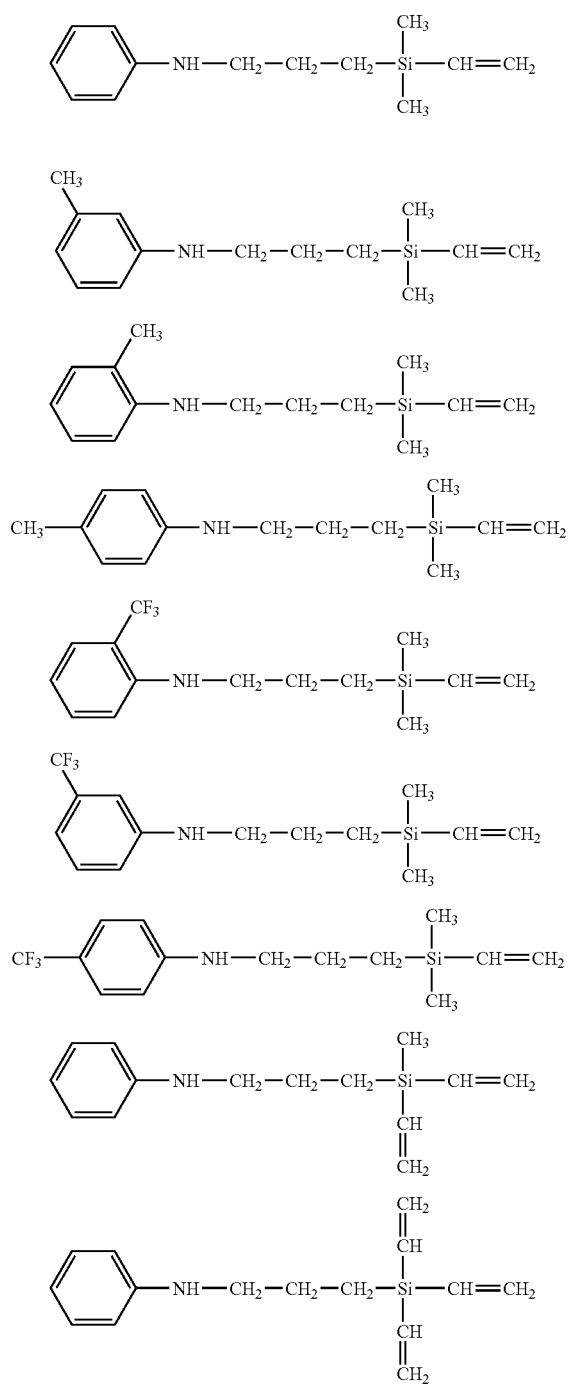

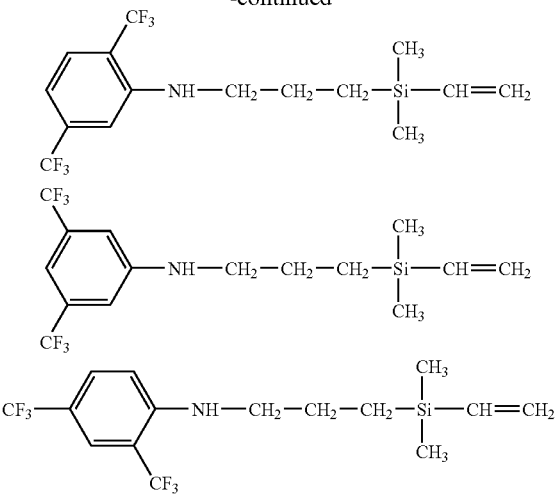

The present compound can be prepared in the following steps.

Step 1

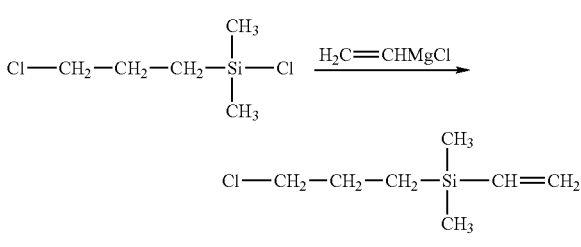

Step 2

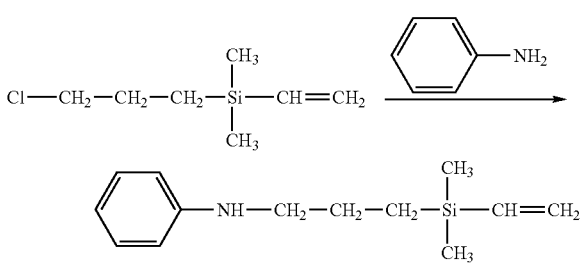

In Step 1, a halogenated silane, such as 3-chloropropyldimethylchlorosilane, is reacted with a Grinard reagent, such as vinyl magnesium chloride, to form 3-chloropropyldimethylvinylsilane. When 3-chloropropylmethyldichlorosilane or 3-chloropropyltrichlorosilane is used as the halogenated silane instead of 3-chloropropyldimethylchlorosilane, 3-chloropropylmethyldivinylsilane or 3-chloropropyltrivinylsilane is obtained, respectively. The reaction is generally carried out by dropwise adding the halogenated silane to a solution of vinyl magnesium chloride in THF. The reaction temperature may be in a range of from 20 to 75 degrees C. The reaction is exothermic. Therefore, if the temperature rises too high, the reaction mixture may be cooled. After the completion of the addition, the reaction mixture is stirred for further 30 minutes to 10 hours. Then, the salt is dissolved in diluted hydrochloric acid and the organic phase is recovered and purified to obtain an intermediate product.

The vinyl silanes obtained in Step 1, such as 3-chloropropyldimethylvinylsilane, is reacted with an aromatic amino compound, such as aniline, to obtain a desired compound. As the aromatic amino compounds, use may be made of o-toluidine, m-toluidine, p-toluidine, 2-aminobenzotrifluoride, 3-aminobenzotrifluoride, 4-aminobenzotrifluoride, 2,3-bis(trifluoromethyl)aniline, 2,4-bis(trifluoromethyl)aniline, and 3,4-bis(trifluoromethyl)aniline. The reaction is carried out by mixing the aromatic amino compound with the 3-chloropropyldimethylvinylsialne and heating the mixture at a temperature of from 70 to 150degrees C. for 1 to 20 hours. Then, a salt with hydrochloric acid is removed and further purified to obtain a desired product.

The thus-obtained organic silicon compound is reacted with another compound such as, for instance, a fluorine-containing compound, so that the organic silicon compound having a highly reactive vinyl group can be bonded with the another compound. For instance, as shown below, the organic silicon compound represented by formula (1) is reacted with a compound represented by the following formula (4) to obtain an amide compound represented by the following formula) (2),

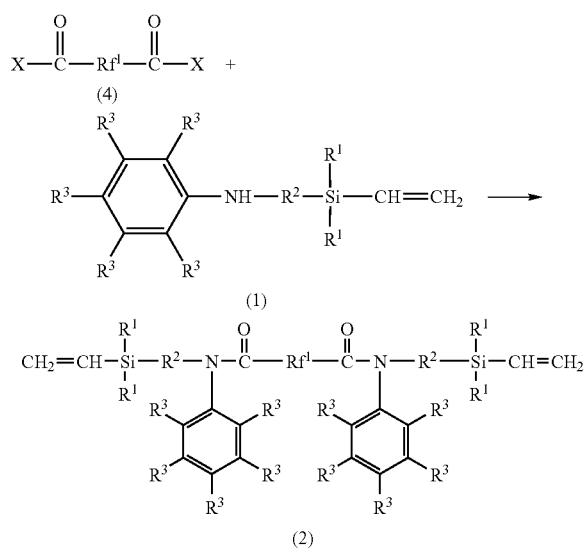

wherein $R^1$ to $R^3$ are as defined above, $Rf^1$ is a perfluoroalkylene group or a divalent perfluoropolyether group, and X is a halogen atom such as a fluorine or chlorine atom.

The amide derivative represented by formula (2) can be prepared by adding 1.0 to 1.2 moles of the organic silicon compound represented by formula (1) per equivalent of the functional group of perfluorodicarboxylic acid halide represented by formula (4) to the acid halide together with an acid-acceptor, such as triethylamine or pyridine, of the same moles as that of the organic silicon compound, while stirring. A reaction temperature is in a range of from room temperature to 100 degrees C. Preferably, the reaction is carried out under heating at a temperature of from 50 to 80 degrees C. for 30 minutes to 3 hours. A solvent such as 1,3-bistrifluorobenzene may be added. After the reaction, 2 to 5 equivalents of calcium carbonate are added and the resulting mixture is heated at 100 degrees C. to 150 degrees C., further subjected to stripping of volatile components under reduced pressure, and filtered for removing solid components to obtain the desired amide compound (2).

When a perfluoromonocarboxylic acid halide represented by the following formula (5) is used instead of the compound represented by formula (4), an amide compound represented by the following formula (3) is obtained,

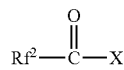

wherein $Rf^2$ is a perfluoroalkyl group or a monovalent perfluoropolyether group and X is a halogen atom such as fluorine or chlorine atom, and

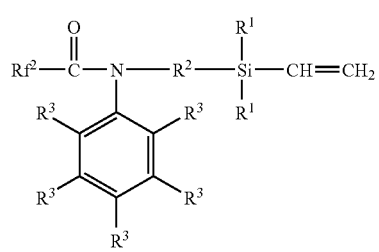

wherein $R^1$ to $R^3$ and $Rf^2$ are as defined above.

The perfluorodicarboxylic acid halide represented by formula (4) and the perfluoromonocarboxylic acid halide represented by formula (5) are known.

The thus-obtained amide derivative of the organic silicon compound, represented by formula (2) or (3), has a highly reactive vinyl group and, therefore, cross linking by hydrosilylation can take place at a lower temperature than that in the prior art.

Examples of $Rf^1$ in the afore-mentioned formulas include the following:

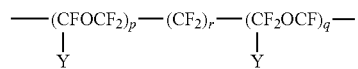

wherein Y is F or $CF_3$, and p, q, and r are integers which satisfy the following equations: $p \geq 0$, $q \geq 0$, $0 \leq p+q \leq 200$, particularly $2 \leq p+q \leq 150$, and $0 \leq r \leq 6$;

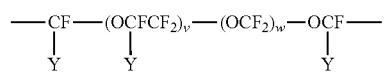

wherein Y is F or $CF_3$, and v and w are integers which satisfy the following equations: $1 \leq v \leq 20$ and $1 \leq w \leq 20$; and

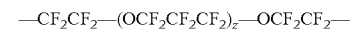

wherein z is an integer which satisfies the following equation: $1 \leq z \leq 100$.

Specific examples of $Rf^1$ include the following.

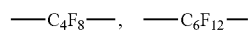
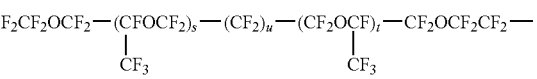

wherein s, t and u are integers which satisfy the following equations: $s \geq 0$, $t \geq 0$, $0 \leq s+t \leq 200$, particularly $2 \leq s+t \leq 150$, and $0 \leq u \leq 6$.

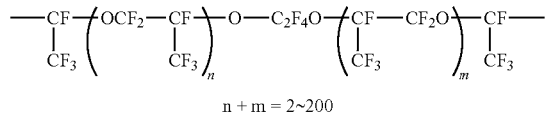

$n + m = 2\sim200$

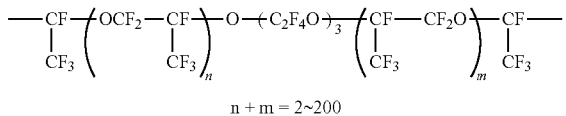

$n + m = 2\sim200$

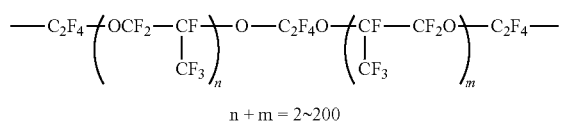

$n + m = 2\sim200$

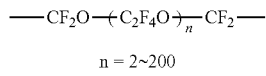

$n = 2\sim200$

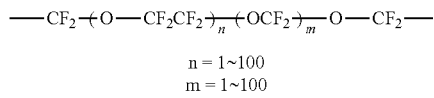

$n = 1\sim100$
$m = 1\sim100$

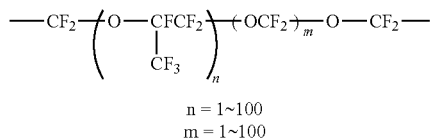

$n = 1\sim100$
$m = 1\sim100$

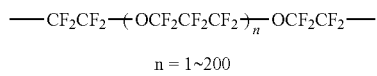

$n = 1\sim200$

Examples of $Rf^2$ in the afore-mentioned formulas include the following.

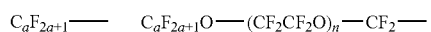

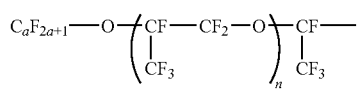

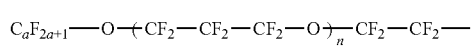

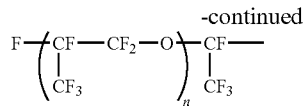

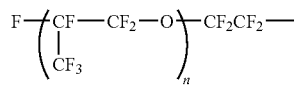

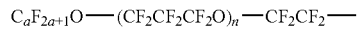

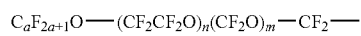

wherein a is an integer of from 1 to 8 and n and m are integers which satisfy the following equations: $0 \leq m \leq 100$, $0 \leq n \leq 100$ and $m+n=0-100$.

The afore-mentioned amide derivative of the organic silicon compound may be hydrosilylated to form a cross-linked product. The cross-linked product is useful as an elastomer and may be used as: diaphragms which need to be chemical resistant and oil resistant and are used in the fields of, for instance, automobile parts, chemical plant parts, parts for OA machine such as copy machines and (ink jet) printers, semiconductor parts, semiconductor manufacturing line, analytical and/or scientific instruments, medical instrument parts, air plane parts, and fuel batteries; rubber molded articles such as valves and sealing parts such as O-rings, oil seals, packings, gaskets, joints, and face seals; gelling materials; adhesives; (sensor) potting materials; tent film materials; sealants; molded parts; extruded parts; covering materials; materials for rolls in copy machines; moisture-preventive coating materials for electricity; laminated rubber cloths; or protecting materials for pressure sensors for automobiles; and materials for protecting electronic components for vehicle installation and for preventing their vibration.

More specifically, the application includes: rubber parts for automobiles, for instance, diaphragms such as diaphragms for fuel regulators, for pulsation dampers, for oil pressure switches, and for EGR, valves such as valves for canisters and for power controlling, O-rings such as O-rings for quick connectors and for injectors, and sealing materials such as oil seals and gaskets for cylinder heads; rubber parts for chemical plants, such as diaphragms for pumps, valves, O-rings, packings, oil seals, and gaskets; rubber parts for ink jet printers and semiconductor manufacturing lines, such as diaphragms, valves, O-rings, packings, and gaskets; rubber parts for analytical and/or scientific instruments and medical instruments, such as diaphragms for pumps, O-rings, packings, valves, and joints; tent film materials; sealants; molded parts; extruded parts; covering materials; materials for rolls in copy machines; moisture-preventive coating materials for electricity; potting materials for sensors; sealing materials for fuel cells; laminated rubber cloths; and rubber parts for air planes, such as O-rings for conduits for fluid conduct such as engine oil for air planes, jet fuels, hydraulic oils and skydrol, face seals, packings, gaskets, diaphragms, and valves.

The present invention will be explained more in detail by reference of the following Examples.

Examples

Example 1

1.3 Litters of a solution of vinyl magnesium chloride in tetrahydrofurane (1 mole/L) was prepared in a two-litter flask, to which 186 grams of 3-chloropropyldimethylchlorosilane was added dropwise with cooling over about 30 minutes. The inner temperature while the addition was from 25 to 35 degrees C. After the completion of the addition, the mixture was left as it was for about 12 hours. The content of the flask was dissolved in diluted hydrochloric acid, an organic phase was separated, washed with water twice, and recovered. The organic phase was distilled to obtain 166 grams of 3-chloropropyldimethylvinylsilane, intermediate product in Step 1. Its boiling point was 70 to 80 degrees C/20 mmHg.

Separately, 254 grams of aniline and 127 grams of toluene were placed in a one-litter flask, heated until the inner temperature became 130 degrees C., to which 150 grams of 3-chloropropyldimethylvinylsilane was added dropwise over about 30 minutes. After the completion of the addition, the mixture was stirred at an inner temperature of 130 to 135 degrees C. for about hours. At the end of the reaction, deposition of white solid was observed. The mixture was cooled to 25 degrees C., to which 250 grams of an aqueous 20% solution of sodium hydroxide were added. Then, an organic phase was separated and distilled to obtain 141 grams of a fraction having a boiling point of 121 to 131 degrees C./1 mmHg. The fraction was subjected to $^1$H-NMR analysis to find out that the fraction was a compound having the following structure, hereinafter referred to as "compound A".

Compound A

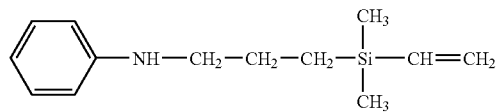

FIG. 1 shows $^1$H-NMR spectra of compound A.

Example 2

360 Grams of the perfluoropolyether having the following structure,

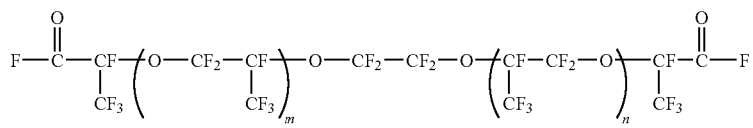

wherein a total of m and n is 95 on average, 11.7 grams of compound A prepared in Example 1, 5.4 grams of triethylamine and 20 grams of 1,3-bis(trifluoromethyl)benzene were mixed and reacted at degrees C. for 2 hours. Then, 7 grams of calcium carbonate powder were added, and the mixture was stirred and heated to 130 degrees C. to strip volatile components. Finally, any remaining volatile components were removed off with nitrogen bubbling at 130 degrees C./5 mmHg. After cooled, 200 grams of perfluorohexane and 3.7 grams of activated carbon were added, stirred, and filtered. 3.7 Grams of synthetic aluminium silicate powder were added to the filtrate, stirred and filtered again. The filtrate obtained was condensed to obtain 335 grams of the polymer having the following structure, hereinafter referred to as "polymer A".

Polymer A

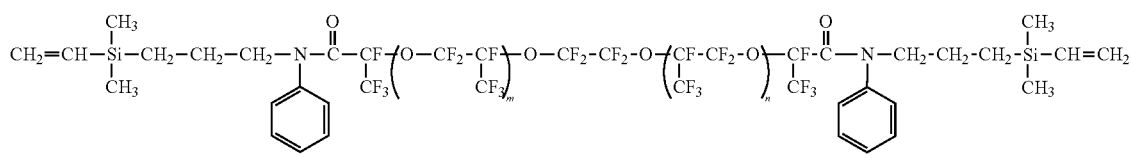

A vinyl number of polymer A as determined by $^1$H-NMR was $1.23 \times 10^{-4}$ mol/g.

FIG. 2 shows $^1$H-NMR spectra of polymer A.

Example 3

345 Grams of the perfluoropolyether having following structure,

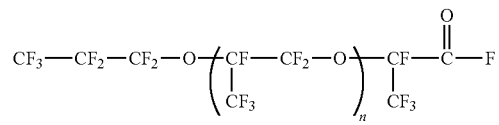

wherein n=23 on average, 18.2 grams of compound A prepared in Example 1, 8.4 grams of triethylamine, and 18.2 grams of 1,3-bis(trifluoromethyl)benzene were mixed and reacted at 70 degrees C. for 2 hours. Then, 9.8 grams of calcium carbonate powder were added, stirred, and heated to 130 degrees C. to strip volatile components. Finally, any remaining volatile components were removed off with nitrogen bubbling at 130 degrees C./5 mmHg. After cooled, 160 grams of perfluorohexane and 3.4 grams of activated carbon were added, stirred, and filtered. 3.4 Grams of synthetic aluminium silicate powder were added to the filtrate, stirred and filtered again. The filtrate obtained was condensed to obtain 344 grams of the polymer having the following structure.

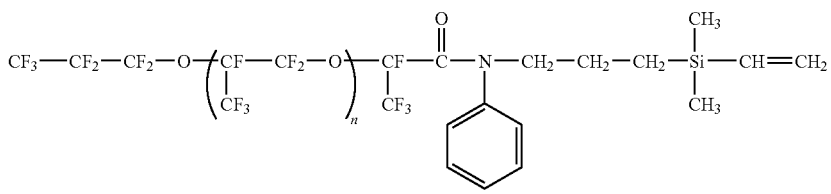

wherein n=23 on average.

Comparative Example 1

The procedures of Example 2 were repeated except that 7.0 grams of allylaniline were used instead of compound A to obtain the polymer having the following structure, hereinafter referred to as polymer B.

Polymer B

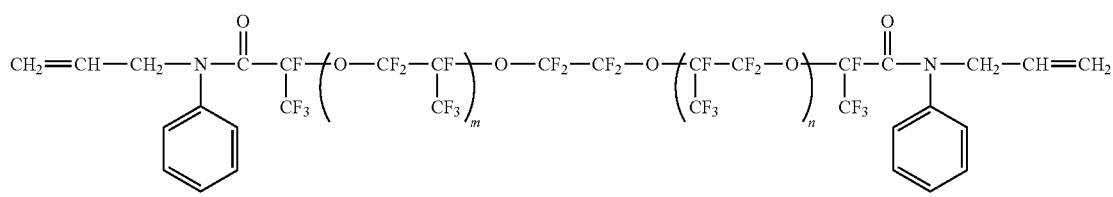

Comparative Example 2

The procedures of Example 2 were repeated except that 10.2 grams of the following compound

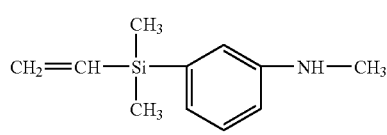

were used instead of compound A to obtain the polymer having the following structure, hereinafter referred to as polymer C.

Polymer C

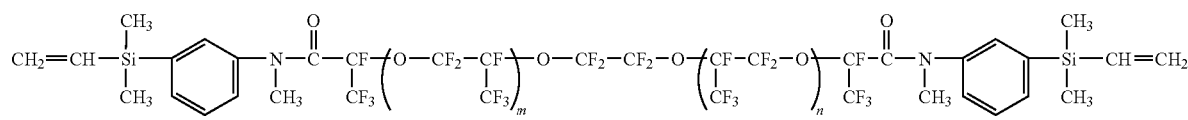

Comparison of Reactivity of the Polymers

Each of polymers A to C was mixed with a cross-linking agent in the amount, in part by mass, shown in the following Table 1 and stirred for homogeneity to prepare compositions 1 to 3. Exothermic peaks in hydrosilylation were determined with DSC and compared.

TABLE 1

| Composition | Part by mass |
|---|---|
| Each of polymers A to C | 100 |
| Si—H cross-linking agent | 3.4 |

TABLE 1-continued

| Composition | Part by mass |
|---|---|
| Platinum catalyst | 0.2 |
| Controlling agent | 0.2 |

The components shown in Table 1 are as follows.

Si—H cross-linking agent: compound having an Si—H, having the following structure.

$$CF_3-CF_2-CF_2-CF_2-CF_2-CF_2-CH_2-CH_2-Si\left(O-\underset{CH_3}{\underset{|}{\overset{CH_3}{\overset{|}{Si}H}}}\right)_3$$

Platinum catalyst: toluene solution of 1,3-divinyl-1,1,3,3-tetramethyldisiloxane platinum complex derived from chloroplatinic acid (platinum content: 0.5%)

Controlling agent: 50% solution of ethynylcyclohexanol in toluene

DSC Determination Conditions

Specimen: 20 to 30 milligrams of the composition is contained in a closed container made of aluminium.

Reference specimen: no composition is contained in the closed container made of aluminium.

Determination was carried out in a nitrogen atmosphere.

Temperature conditions: raised from 25 degrees C. to 200 degrees C. at a rate of 10 degrees C./minute.

Temperatures at the exothermic peak top are shown in Table 2. DSC charts for compositions 1 to 3 are shown in FIG. 3.

TABLE 2

| Composition | Polymer | Temperature of exothermic peak top, °C. |
|---|---|---|
| 1 | Polymer A | 84.7 |
| 2 | Polymer B | 142 |
| 3 | Polymer C | 93.3 |

As seen from Table 2, the exothermic peak of polymer A due to hydrosilylation is observed at a lower temperature than those of polymers B and C and, thus, the reactivity of polymer A is highest.

INDUSTRIAL APPLICABILITY OF THE INVENTION

The present organic silicon compound is useful for preparing a compound which can be cross-linked via hydrosilylation. It is possible to obtain a compound which can be cross-linked at a lower temperature than those of the conventional ones. A cross-linked product of the obtained compound is useful as an elastomer.

The invention claimed is:

1. An amide derivative represented by the following formula:

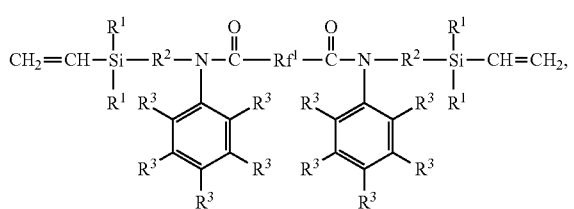

wherein $R^1$ is, independently of each other, a vinyl group or an alkyl group having 1 to 4 carbon atoms, $R^2$ is an alkylene group having 3 to 6 carbon atoms, $R^3$ is, independently of each other, a hydrogen atom or an alkyl group having 1 to 4 carbon atoms and optionally substituted with one or more fluorine atoms, and $Rf^1$ is a perfluoroalkylene group or a divalent perfluoropolyether group.

2. An amide derivative represented by the following formula:

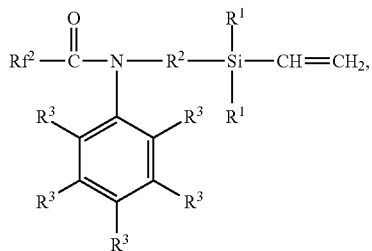

wherein $R^1$ is, independently of each other, a vinyl group or an alkyl group having 1 to 4 carbon atoms, $R^2$ is an alkylene group having 3 to 6 carbon atoms, $R^3$ is, independently of each other, a hydrogen atom or an alkyl group having 1 to 4 carbon atoms and optionally substituted with one or more fluorine atoms, and $Rf^2$ is a perfluoroalkyl group or a monovalent perfluoropolyether group.

3. An elastomer formed by crosslinking an amide derivative represented by the following formula

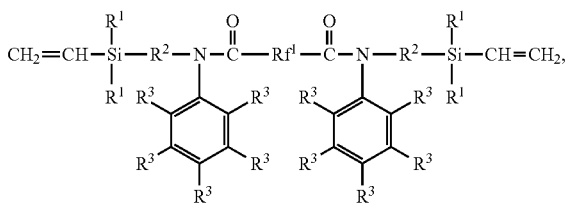

wherein $R^1$ is, independently of each other, a vinyl group or an alkyl group having 1 to 4 carbon atoms, $R^2$ is an alkylene group having 3 to 6 carbon atoms, $R^3$ is, independently of each other, a hydrogen atom or an alkyl group having 1 to 4 carbon atoms and optionally substituted with one or more fluorine atoms and $Rf^2$ is a perfluoroalkylene group or a divalent perfluoropolyether group.

* * * * *